(12) United States Patent
Mulrooney et al.

(10) Patent No.: US 10,814,125 B2
(45) Date of Patent: Oct. 27, 2020

(54) CATHETER

(71) Applicant: Phagenesis Limited, Manchester, Greater Manchester (GB)

(72) Inventors: Conor Mulrooney, Manchester (GB); Steve Bookbinder, Manchester (GB)

(73) Assignee: Phagenesis Limited, Greater Manchester (GB)

( * ) Notice: Subject to any disclaimer, the term of this patent is extended or adjusted under 35 U.S.C. 154(b) by 133 days.

(21) Appl. No.: 15/749,952

(22) PCT Filed: Aug. 4, 2016

(86) PCT No.: PCT/GB2016/052390
§ 371 (c)(1),
(2) Date: Feb. 2, 2018

(87) PCT Pub. No.: WO2017/021732
PCT Pub. Date: Feb. 9, 2017

(65) Prior Publication Data
US 2018/0221649 A1 Aug. 9, 2018

(30) Foreign Application Priority Data
Aug. 4, 2015 (GB) .................................. 1513797.9

(51) Int. Cl.
*A61N 1/05* (2006.01)
*A61B 90/00* (2016.01)
(Continued)

(52) U.S. Cl.
CPC ................ *A61N 1/05* (2013.01); *A61B 90/06* (2016.02); *A61B 90/08* (2016.02); *A61N 1/0519* (2013.01);
(Continued)

(58) Field of Classification Search
CPC .......... A61N 1/05; A61B 90/00; A61B 90/06; A61B 90/08
See application file for complete search history.

(56) References Cited

U.S. PATENT DOCUMENTS

| 5,836,895 A | 11/1998 | Ramsy, III |
| 2005/0059890 A1* | 3/2005 | Deal ................. A61M 25/0029 600/433 |

(Continued)

FOREIGN PATENT DOCUMENTS

| CN | 2033089196 U | 1/2014 |
| CN | 203954394 U | 11/2014 |

(Continued)

OTHER PUBLICATIONS

International Search Report for Appl No. GB1513792.0 dated Jan. 4, 2016, 4 pages.

(Continued)

*Primary Examiner* — Christopher J Beccia
(74) *Attorney, Agent, or Firm* — Maine Cernota & Rardin

(57) ABSTRACT

A catheter comprising a proximal end, a distal end and a pair of electrodes spaced apart between the proximal and distal ends; and a catheter guide comprising i) a first positioning indicator distal to the pair of electrodes for indicating if the catheter needs inserting further into the patient; and ii) a second positioning indicator proximate the first positioning indicator for indicating correct positioning of a catheter.

17 Claims, 1 Drawing Sheet

(51) Int. Cl.
　　　*A61M 25/00*　　(2006.01)
　　　*A61B 1/24*　　　(2006.01)
　　　*A61M 25/01*　　(2006.01)

(52) U.S. Cl.
　　　CPC ........... *A61B 1/24* (2013.01); *A61B 2090/062* (2016.02); *A61B 2090/0807* (2016.02); *A61M 25/0105* (2013.01); *A61M 2025/0008* (2013.01); *A61M 2025/0166* (2013.01)

(56) References Cited

U.S. PATENT DOCUMENTS

| | | | |
|---|---|---|---|
| 2005/0274384 A1* | 12/2005 | Tran | A61M 25/0102 128/831 |
| 2006/0052766 A1 | 3/2006 | Patel | |
| 2010/0115739 A1 | 5/2010 | Mathur | |
| 2010/0170066 A1 | 7/2010 | Honeycutt | |
| 2011/0210215 A1 | 9/2011 | Nitsche et al. | |
| 2014/0288384 A1* | 9/2014 | Mulrooney | A61M 25/00 600/301 |
| 2015/0099935 A1* | 4/2015 | Runnels | A61M 16/0488 600/188 |

FOREIGN PATENT DOCUMENTS

| | | |
|---|---|---|
| CN | 204319485 U | 5/2015 |
| EP | 11779307 A2 | 2/2013 |
| JP | 2014068716 A | 4/2014 |
| WO | 2005115234 A1 | 12/2005 |
| WO | 2006024825 A1 | 3/2006 |
| WO | 2012131303 A1 | 10/2012 |
| WO | 2015013770 A1 | 2/2015 |

OTHER PUBLICATIONS

International Search Report for Appl No. GB1521538.7 dated Mar. 29, 2016, 5 pages.
International Search Report for Appl No. GB1513797.9 dated Jan. 19, 2016, 3 pages.
PCT Search Report for PCT Application No. PCT/GB2016/052390, dated Oct. 26, 2016, 15 pages.
Great Britain Search Report for GB Application No. 15137979, dated Jan. 19, 2016, 3 pages.

* cited by examiner

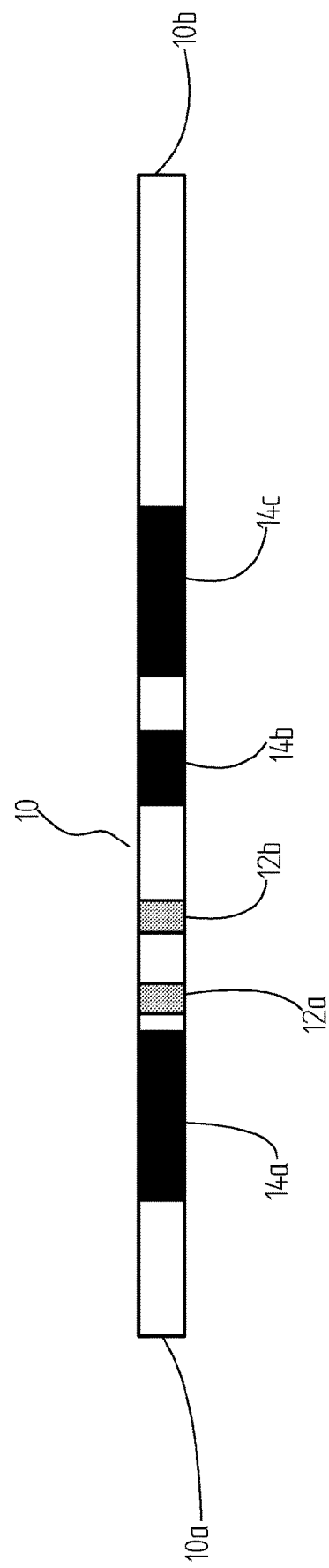

CATHETER

RELATED APPLICATIONS

This application is a national phase application filed under 35 USC § 371 of PCT Application No. PCT/GB2016/052390 with an International filing date of Aug. 4, 2016, which claims priority of GB Patent Application GB 1513797.9 filed Aug. 4, 2015. Each of these applications is herein incorporated by reference in its entirety for all purposes.

FIELD OF THE INVENTION

The present invention describes a catheter suitable for positioning specific components of a catheter such that they are aligned with one or more defined positions within a patient.

BACKGROUND OF THE INVENTION

Catheters are known in the prior art that comprise electrodes for the purpose of application of electrical stimulation to a patient's pharynx in order to aid recovery from neurogenic dysphagia. WO2006/024825 describes the general concept of using a catheter to apply electrical stimulation to a patient's pharynx. WO2012/131303 describes a catheter having a pair of spaced apart electrodes.

Both WO2006/024825 and WO2012/13103 are hereby incorporated by reference.

Electropharyngeal stimulation to treat dysphagia requires the positioning of electrodes in a defined region of a patient's pharynx in order to target specific nerve clusters. WO2012/131303 describes a printed positioning guide on the catheter that is aligned with the entrance to a patient's nostrils in an attempt to accurately locate the pair of electrodes in the target pharyngeal region. However it has now been determined that, due to anatomical variations between patients, and the possibility of deflection of the catheter as it is fed through the patient's nasal passageway, it is not always possible to reliably confirm the position of the pair of electrode's relative to the target region of the patient's pharynx using the positioning guide disclosed in WO2012/131303.

For the purposes of electrical stimulation of the pharynx to treat oropharyngeal dysphagia, the target region is in a vertical position equivalent to the junction between the C3 and C4 cervical vertebrae. The midpoint between two electrodes should be positioned vertically to align with the point between the C3 and C4 vertebrae.

It is possible to examine the body of a catheter passed transnasally, via an oral examination, once the catheter has passed through the oral spaces into the laryngopharynx. With the patients mouth open and tongue depressed it is possible to see a small area of the posterior wall of the oropharynx though the fauces on either side of the uvula. If a catheter is passed through this region a small section of the catheter can be seen against the posterior pharyngeal wall.

The part of the pharynx that can be directly visualised in this way however corresponds to the upper section of the C3 vertebra. It is not possible to see part of the pharynx that corresponds to the C3:C4 junction as this is located further down out of the direct line of sight. As such the electrodes cannot be located correctly by direct oral visual examination.

Another challenge in using an oral exam to correctly position the catheter in the pharynx is that features of the catheter may be difficult to visualise or differentiate due to limited visibility of the pharynx, low light, patient discomfort and catheter movement during exam.

There are a number of possible outcomes that can occur on initial insertion of the catheter:

a) Anatomically, the patient presents a long internal path from nares to the lower oropharynx. When the catheter is inserted the presumed correct distance, the electrodes are still positioned above the target area. The electrodes may or may not be visible through oral exam;

b) As per outcome a) above but with the added complication that the catheter is deflected upwards as it passes through the nasal cavity thus taking a longer path with the result that the electrodes are vertically positioned even higher above the target region than desired. The electrodes may or may not be visible through oral exam.

c) Anatomically the patient presents a short internal path from nares to the lower oropharynx. When the catheter is inserted the presumed correct distance the electrodes end up positioned below the target area

SUMMARY OF THE INVENTION

The present invention seeks to address the aforementioned problems and provide an improved catheter guide and method of positioning a catheter within a patient such that a pair of electrodes are aligned correctly to a target region within the patient regardless of anatomical variation or internal deflection.

An aspect of the invention provides a catheter comprising a proximal end, a distal end and a pair of electrodes spaced apart between said proximal and distal ends; and a catheter guide comprising i) a first positioning indicator distal to the pair of electrodes for indicating if the catheter needs inserting further into the patient; and ii) a second positioning indicator proximate to the electrodes for indicating correct positioning of a catheter In use the catheter would be inserted transnasally and initially positioned with the positioning guide as described in WO2012/131303 located at the entrance to the nostrils. The catheter of the present invention then allows a suitably trained healthcare operator to first check whether the electrodes on the inserted catheter are in the correct position and if not to make adjustments to the catheter in a directed way to move them to the correct position. By looking into the patient's mouth and depressing the patient's tongue, the operator is able to view a small area of the posterior wall of the oropharynx framed by the patient's uvula, tonsils and tongue. The operator will also be able to see the section of the inserted catheter located in this area.

If on the visible section of catheter the operator is able to see the second positioning indicator, then no further adjustment is required, as the electrodes will be positioned correctly adjacent to the C3:C4 junction.

If the operator is able to see the electrodes, or the first positioning indicator, they know that they need to insert the catheter further into the patient. The operator will continue to insert the catheter incrementally via the nostrils until such time as the second positioning indicator becomes visible. The catheter is then fixed in position.

The positioning guide may further comprise a third positioning indicator for indicating if the catheter has been inserted too far into the patient.

If the operator is able to see the third positioning indicator, but not the second positioning indicator, then they know they need to withdraw the catheter. The operator will withdraw the catheter incrementally via the nostril until such time as the second positioning indicator becomes visible. The catheter is then fixed in position.

The first positioning indicator may be a distal block forming a continuous pattern, colour or consistent visual appearance extending a number of centimetres distally from the electrode pair and around the diameter of the catheter.

The third positioning indicator may be a proximal block forming a continuous pattern, colour or consistent visual appearance extending a number of centimetres proximally from the electrode pair and around the diameter of the catheter that is readily distinguishable from that of the distal block.

The second positioning indicator forms a pattern, colour or visual appearance that extends around the diameter of the catheter that is readily distinguishable from both the distal block and the proximal block.

The first, second and third positioning indicators may be distinguished from each other by colour or by pattern.

Visualisation of the first, second and third positioning indicators may be facilitated through the use of an external light source.

The first, second and third positioning indicators may be reactive or reflective when illuminated via an external light source to better locate or differentiate between the guides and/or the correct position indicator.

The first, second and third positioning indicators may be luminescent or fluorescent.

Use of a luminescent or fluorescent positioning guide is advantageous as it may be seen in the dark region of the patient's pharynx by a medical physician without the need for an external light source.

The first, second and third positioning indicators may actively emit light transmitted for example from an externally located source via a fibre optic channel.

Use of an active light source as a positioning guide is advantageous as it may be seen in the dark region of the patient's pharynx by a medical physician without the need for an external light source.

A further aspect of the invention provides a method of positioning a catheter for treatment of dysphagia in a patient, the method comprising: i) providing a catheter having a pair of electrodes spaced apart between a distal end and a proximal end of the catheter, ii) providing a catheter guide on the catheter, the catheter guide comprising a first positioning indicator distal to the pair of electrodes for indicating if the catheter needs inserting further into the patient and a second positioning indicator proximate to the electrodes for indicating correct positioning of the catheter and a third positioning indicator proximate to the second positioning indicator for indicating the catheter has been inserted too far iii) inserting the catheter into a patient nasally and if required adjusting it thereafter to the extent that only the second positioning indicator, but not the first positioning indicator or the third positioning indicator, is visible by way of oral examination.

BRIEF DESCRIPTION OF THE DRAWINGS

The invention will now be described by way of reference to the following drawing:

FIG. 1 shows a catheter according to a first embodiment of the invention.

DETAILED DESCRIPTION

Referring to FIG. 1, a catheter 10 for use in treatment of dysphagia has a distal end 10a and a proximal end 10b. A pair of electrodes 12a, 12b is positioned between the distal end 10a and the proximal end 10b of the catheter 10 in a spaced apart arrangement. Each electrode 12a, 12b is three millimetres wide and the pair of electrodes is spaced apart by ten millimetres. A first positioning indicator 14a, for use as in identifying if the catheter 10 has not been inserted far enough into the patient, is positioned distal to the pair of electrodes 12a, 12b. A second positioning indicator 14b, used for identifying correct positioning of the catheter 10, is positioned proximate to the first positioning guide 14a and proximate to the electrodes. In the illustrated embodiment a third positioning indicator 14c, used for identifying if the catheter 10 has been inserted too far into the patient, is positioned proximate to the second positioning indicator 14b.

In an embodiment of the invention the first positioning guide 14a comprises one or more markers or bands forming a continuous colour, patter or visual appearance around the circumference of the catheter and which extend around the perimeter of the catheter 10 in a proximal direction away from the pair of electrodes 12a, 12b. The second positioning guide 14b comprises one or more markers or bands forming a continuous colour, pattern or visual appearance, different to the colour, pattern or visual appearance of the first positioning indicator, around the circumference of the catheter 10 and which extend around the perimeter of the catheter 10 in a proximal direction away from the first positioning indicator 14a. The third positioning indicator 14c comprises one or more markers or bands forming a continuous colour, pattern or visual appearance, different to the colour, pattern or visual appearance of the second positioning indicator, around the circumference of the catheter 10 and which extend around the perimeter of the catheter 10 in a proximal direction away from the second positioning indicator 14b.

The first, second and third positioning indicators 14a, 14b, 14c in certain embodiments are luminescent or fluorescent markers or bands positioned on the surface of the catheter 10. Alternatively, the first, second and third positioning indicators 14a, 14b, 14c can be markers or bands positioned on the surface of the catheter 10 and reactive to light. The first, second and third positioning indicators 14a, 14b, 14c can be formed from an ink, film, coating, surface treatment or material property.

In certain embodiments (not shown), the catheter 10 comprises an outer sleeve and an inner tube. The pair of electrodes 12a, 12b is positioned on the outer surface of the outer sleeve which is formed from a transparent material. The first, second and third positioning indicators 14a, 14b 14c are positioned on the outer surface of the sleeve. In certain embodiments the inner tube is a feeding tube.

In certain embodiments, the catheter 10 has a printed nasal positioning guide (not shown but as described in WO2012/131303) on its outer surface. The printed nasal positioning guide enables a medical physician to roughly position the catheter 10 by aligning an appropriate marker on the printed positioning guide with the entrance to the patient's nostrils. In use, the catheter 10 is inserted through a patient's nostrils and fed towards the patient's pharynx until such time as a nasal positioning guide is located at the entrance to the nostrils. By depressing the patient's tongue, a medical physician then has a clear view of a space at the back of the patient's mouth which is defined by the uvula, tonsils and tongue. In this space the medical physician will be able to see the first, second or third positioning guides 14a, 14b, 14c, depending on the position of the catheter 10 once inserted. If the medical physician can see the pair of electrodes 12a, 12b or the first positioning indicators 14a, the medical professional will know that he needs to insert the catheter 10 further into the patient. If the medical professional can see the second positioning indicator 14b, the medical professional will know the catheter 10 is correctly positioned. If the medical professional can only see the third positioning guide 14c, the medical professional will know that the catheter 10 needs withdrawing from the patient until the second positioning indicator 14c is visible.

If the first, second and third positioning indicators 14a, 14b, 14c are luminescent or fluorescent markers or bands, the first, second and third positioning indicators 14a, 14b, 14c will be self-illuminating and the medical physician would be able to position the catheter 10 without the aid of an external light source. If the first, second and third positioning indicators 14a, 14b, 14c are markers or bands which are reactive to light, the medical physician may require an external light source in order to identify the position of the first, second and third positioning indicators 14a, 14b, 14c.

The invention claimed is:

1. A catheter comprising a proximal end, a distal end and a pair of electrodes spaced apart between said proximal and distal ends; a first catheter guide comprising markers configured to be aligned with the entrance to a patient's nostrils to roughly position the pair of electrodes for treatment of a specific, predefined condition; and a second catheter guide comprising i) a first positioning indicator distal to the pair of electrodes configured to indicate if the catheter needs inserting further into the patient following an initial insertion thereof into the patient to treat the specific, predefined condition; and ii) a second positioning indicator proximate the first positioning indicator configured to indicate correct positioning of a catheter for treatment of the specific, predefined condition following the initial insertion thereof into a patient, wherein the first positioning indicator and second positioning indicator are configured to indicate improper and proper placement of the catheter for the treatment of the specific, predefined condition, respectively, when viewed directly through a patient's oral cavity.

2. The catheter according to claim 1 wherein the first positioning indicator comprises a first marker or band having a first visual characteristic and which extends continuously around the circumference of the catheter.

3. The catheter according to claim 1 wherein the second positioning indicator comprises a second marker or band having a second visual characteristic, different to the first visual characteristic, and which extends around the circumference of the catheter.

4. The catheter according to claim 1 wherein the catheter guide further comprises a third positioning indicator proximate the second positioning indicator configured to indicate if the catheter has been inserted too far into a patient.

5. The catheter according to claim 4, wherein the third positioning indicator comprises a third marker or bands having a third visual characteristic, different to the second visual characteristic, and which extends around the circumference of the catheter.

6. The catheter according to claim 1 wherein the catheter guide is located on the surface of the catheter.

7. The catheter according to claim 1, wherein said catheter is configured for treating dysphagia.

8. The catheter according to claim 1 wherein the catheter guide is used as a visual positioning aid.

9. The catheter according to claim 4 wherein one or more of the first positioning indicator, second positioning indicator and third positioning indicator is luminescent or fluorescent.

10. The catheter according to claim 4 wherein one or more of the first positioning indicator, second positioning indicator and third positioning indicator is reactive or reflective in the presence of a light source.

11. The catheter according to claim 1 wherein one or more of the first positioning indicator, second positioning indicator and third positioning indicator is formed from an ink, film, coating, surface treatment or material property.

12. The catheter according to claim 11 wherein one or more of the first positioning indicator, second positioning indicator and third positioning indicator is reactive or reflective in the presence of white light, coloured light or ultraviolet light.

13. A method of positioning a catheter for treatment of dysphagia in a patient, the method comprising: i) providing a catheter having a pair of electrodes spaced apart between a distal end and a proximal end of the catheter, ii) providing a first catheter guide on the catheter comprising markers configured to be aligned with the entrance to a patient's nostrils to roughly position the pair of electrodes for treatment of a specific, predefined condition iii) providing a second catheter guide on the catheter, the second catheter guide comprising: a first positioning indicator distal to the pair of electrodes configured to indicate if the catheter needs inserting further into the patient to treat the specific, predefined condition and a second positioning indicator proximate the first positioning guide configured to indicate correct positioning of the catheter for treatment of the specific, predefined condition; iii) inserting the catheter into a patient nasally to the extent that the marker is aligned with the entrance to a patient's nostrils and then, by way of direct, oral examination, adjusting the catheter such that only the second positioning indicator, but not the first positioning indicator, is visible against a backdrop comprising an area of the posterior wall of the oropharynx framed by the patient's uvula, tonsils and tongue.

14. The method of positioning a catheter according to claim 13, the method comprising the further step of directing a light into the patient's mouth to illuminate the catheter guide.

15. A catheter, the catheter comprising:
a proximal end, a distal end and a pair of electrodes spaced apart between said proximal and distal ends;
a first catheter guide comprising markers configured to be aligned with the entrance to a patient's nostrils to roughly position the pair of electrodes for treatment of a specific, predefined condition; and
a second catheter guide consisting of i) a first positioning indicator distal to the pair of electrodes configured to indicate if the catheter needs inserting further into the patient to treat the specific, predefined condition; and ii) a second positioning indicator proximate the first positioning indicator configured to indicate correct positioning of the catheter for treatment of the specific, predefined condition wherein the first positioning indicator and second positioning indicator are configured for viewing directly through a patient's oral cavity against a backdrop comprising an area of the posterior wall of the oropharynx framed by the patient's uvula, tonsils and tongue.

16. The catheter according to claim 1 wherein when the second positioning indicator is visible through a patient's oral cavity, the first positioning indicator is not.

17. The catheter according to claim 1 wherein the first positioning indicator and second positioning indicator are configured to indicate improper and proper placement of the catheter, respectively, when viewed against an area of the posterior wall of the oropharynx framed by the patient's uvula, tonsils and tongue.

\* \* \* \* \*